US012622691B2

(12) United States Patent
Norenstam

(10) Patent No.: US 12,622,691 B2
(45) Date of Patent: May 12, 2026

(54) CRIMPING DEVICE AND METHOD

(71) Applicant: Suturion AB, Ramlösa (SE)

(72) Inventor: Rickard Norenstam, Löddeköpinge (SE)

(73) Assignee: Suturion AB, Ramlösa (SE)

( * ) Notice: Subject to any disclaimer, the term of this patent is extended or adjusted under 35 U.S.C. 154(b) by 76 days.

(21) Appl. No.: 18/417,642

(22) Filed: Jan. 19, 2024

(65) Prior Publication Data

US 2025/0235207 A1     Jul. 24, 2025

(51) Int. Cl.
*A61B 17/06* (2006.01)

(52) U.S. Cl.
CPC .. *A61B 17/06004* (2013.01); *A61B 17/06066* (2013.01); *A61B 2017/06047* (2013.01); *A61B 2017/0609* (2013.01)

(58) Field of Classification Search
CPC .. A61B 2017/0609; A61B 2017/06047; A61B 2017/0472; A61B 17/0469; A61B 17/06004; A61B 17/06066
USPC ........... 29/712, 515, 505, 428, 465, 243.58, 29/243.57
See application file for complete search history.

(56) References Cited

U.S. PATENT DOCUMENTS

| | | | | |
|---|---|---|---|---|
| 5,230,352 A | * | 7/1993 | Putnam | B21K 21/12 |
| | | | | 223/102 |
| 5,553,477 A | | 9/1996 | Eisensmith | |
| 6,322,582 B1 | | 11/2001 | Richard et al. | |
| 2021/0378660 A1 | | 12/2021 | Börner | |

FOREIGN PATENT DOCUMENTS

| | | |
|---|---|---|
| CN | 108421909 A | 8/2018 |
| EP | 3922189 A1 | 12/2021 |

* cited by examiner

*Primary Examiner* — Tuan V Nguyen
(74) *Attorney, Agent, or Firm* — DINSMORE & SHOHL LLP

(57) ABSTRACT

A crimping device for securing a suture to a double-pointed medical suture needle includes a lower block and an upper block that are pressed towards each other to secure the suture to the needle. The lower block has a first groove to accommodate the suture and a second groove to accommodate the needle. The grooves are substantially perpendicularly to each other. The lower block has a lower crimping pin in a lower crimping pin channel at an intercept of the first and second groove. The upper block has an upper crimping pin arranged in an upper crimping pin channel at the intercept of the grooves. The lower and upper crimping pins are configured to move in the lower and upper crimping pin channels, respectively, towards the groove intercept to secure the suture to the needle. A method of securing a suture to a double-pointed medical suture needle is also disclosed.

18 Claims, 7 Drawing Sheets

CRIMPING DEVICE AND METHOD

The present disclosure relates to a method and a crimping device for securing a suture to a double-pointed medical suture needle.

BACKGROUND OF INVENTION

Surgical needles come in a number of variants and are used for a number of purposes, ranging from simple closure of wounds to advanced surgery.

Eyed needles, which are often reusable and supplied separate from their suture thread, are often used for suturing. The suture must be threaded on site, which is a time-consuming task. One advantage, however, is that a number of different thread and needle combinations are possible.

A swaged needle is typically supplied as a pre-packed eyeless needle attached to a specific length of suture thread. One advantage of this is that the medical staff does not have to spend time on threading the suture on the needle. A further advantage is that the needle end and suture are joined as a continuous unit, which minimizes trauma to tissue during suturing. A swaged needle may have one pointed end and one hollow end, in which the suture is placed and secured.

In some surgical procedures, for example, open surgical procedures, the wound may be closed using a suturing device with built-in needle-transfer of a double-pointed needle. In these devices, a double-pointed needle is transferred between two jaws, preferably in an automatic fashion by opening and closing the jaws repeatedly, to close the wound.

The process of crimping the suture to the double-pointed needle requires precision both in terms how much pressure is applied and where the pressure is applied.

EP 3 922 189 A1 discloses a crimping device for securing a suture to a double-pointed medical suture needle. The crimping device has a lower block and an upper block that can be pressed against each other to secure the suture to the double-pointed medical suture needle. Each of the lower block and upper block comprise a first grove and a second groove. The second groove comprises a protrusion at an intercept of the first groove and second groove to deform the double-pointed medical suture needle.

While the device described in EP 3 922 189 A1 is functional, the inventors of the presently described crimping device have estimated that there is room for further improvements to further increase the precision of the crimping device.

SUMMARY OF INVENTION

The present disclosure relates to an improved crimping device for securing a suture to a double-pointed medical suture needle.

According to a first embodiment, the crimping device for securing a suture to a double-pointed medical suture needle comprises:

a lower block and an upper block that can be pressed towards each other to secure the suture to the double-pointed medical suture needle, the lower block comprising:

a first groove configured to accommodate the suture;

a second groove configured to accommodate the double-pointed medical suture needle, the first and second grooves arranged substantially perpendicularly to each other, wherein the lower block comprises a lower crimping pin arranged in a lower crimping pin channel at an intercept of the first groove and the second groove;

wherein the upper block comprises an upper crimping pin arranged in an upper crimping pin channel at the intercept of the first groove and the second groove;

wherein the lower crimping pin and the upper crimping pin are configured to be moved in the lower crimping pin channel and the upper crimping pin channel, respectively, towards the intercept of the first groove and second groove to secure the suture to the double-pointed medical suture needle.

By having a lower crimping pin in a lower crimping pin channel and an upper crimping pin in an upper crimping pin channel, the double-pointed medical suture needle can be crimped very precisely at a through-hole of the double-pointed medical suture needle for the suture.

Preferably, the lower and upper crimping pin each have a pointed end towards the intercept of the first groove and second groove. The pointed ends may cause a deformation of the double-pointed medical suture needle to bond the suture to the double-pointed medical suture needle in a very precise manner.

Preferably, the lower block and the upper block are adapted to hold the double-pointed medical suture needle in a locked position when the lower block and the upper block are pressed towards each other. This can be done, for example, by having a second groove configured to accommodate the double-pointed medical suture needle and a part of the upper block configured to assert a force on the double-pointed medical suture needle to lock in the second groove.

The second groove in the lower block may have a cross-section having a tapered shape being progressively smaller with reference from a side facing the upper block, preferably wherein the cross-section is substantially V-shaped. The upper block may comprise at least one needle holder element facing the lower block, which is adapted to lock the double-pointed medical suture needle in a locked position when the lower block and the upper block are pressed towards each other. The at least one needle holder element may be in integral part of the upper block. It may thus be seen as a needle holder portion of the upper block.

The crimping device may further comprise a secondary lower block arranged on an exterior side of the lower block and secondary upper block arranged on an exterior side of the upper block. The lower crimping pin and upper crimping may be fixed to the secondary lower block and secondary upper block, respectively. The secondary lower block and secondary upper block may then be controlled to control the movement of the lower crimping pin and upper crimping in the lower block and upper block, respectively. A lower spring arranged between the lower block and the secondary lower block and an upper spring arranged between the upper block and the secondary upper block may be used to control movement of the lower crimping pin and upper crimping pin.

The lower crimping pin and/or the upper crimping pin may have first threads engaging with second threads of the secondary lower block and the secondary upper block, respectively. The lower crimping pin can thereby be configured to an exact fixed position relative to the secondary lower block. This mechanism can be used to calibrate how much the lower crimping pin can protrude from the lower block to deform the double-pointed medical suture needle. The mechanism enables very precise deformation of the double-pointed medical suture needle. The protrusion of the upper crimping pin can be calibrated in the same way as the lower crimping pin.

The present disclosure further relates to a method of securing at least one suture to at least one double-pointed medical suture needle, comprising the steps of:

threading the double-pointed medical suture needle by inserting the suture through a through-hole of the double-pointed medical suture needle;

providing a crimping device having a lower block and an upper block, each of the lower block and the upper block comprising a first groove configured to accommodate the suture; and a second groove configured to accommodate the double-pointed medical suture needle, the first and second grooves arranged substantially perpendicularly to each other, wherein the second groove comprises a protrusion at an intercept of the first groove and second groove;

placing the double-pointed medical suture needle in the second groove and the suture in the first groove; and crimping the double-pointed medical suture needle by pressing the lower block and the upper block together, thereby securing the suture to the double-pointed medical suture needle.

A person skilled in the art will recognize that the presently disclosed method of securing a suture to a double-pointed medical suture needle may be performed using any embodiment of the presently disclosed crimping device for securing a suture to a double-pointed medical suture needle.

DESCRIPTION OF DRAWINGS

Various embodiments are described hereinafter with reference to the drawings. The drawings are examples of embodiments and are intended to illustrate some of the features of the presently disclosed crimping device for securing a suture to a double-pointed medical suture needle, and are not limiting to the presently disclosed crimping device for securing a suture to a double-pointed medical suture needle.

DETAILED DESCRIPTION OF THE INVENTION

Figure 1:
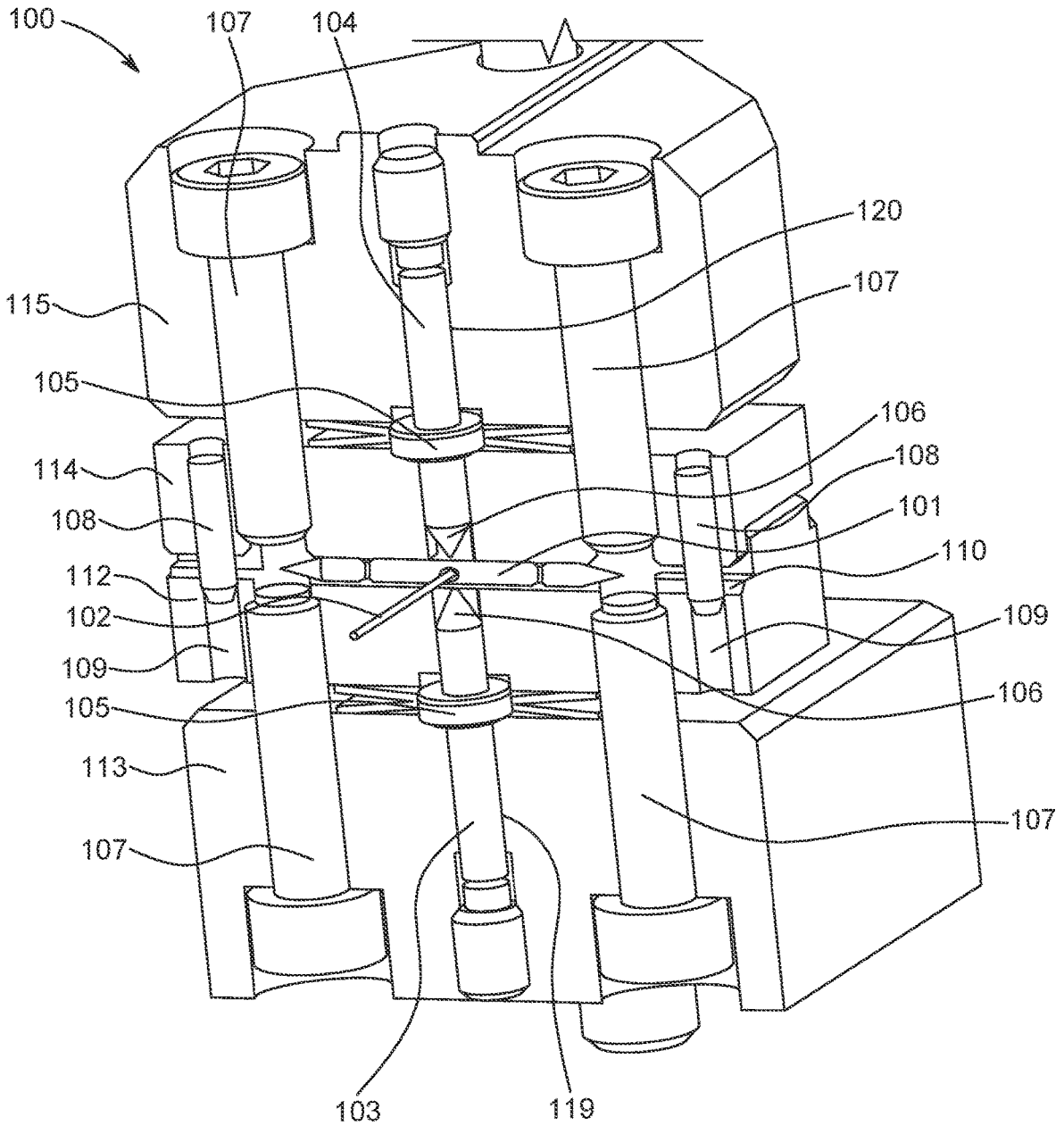
FIG. 1 shows an example of a the presently disclosed crimping device.

The present disclosure relates to a crimping device for securing a suture to a double-pointed medical suture needle. Such a needle has a through-hole for the suture somewhere on the needle body between the two ends. The crimping device comprises a lower block and an upper block that can be pressed towards each other to secure the suture to the double-pointed medical suture needle. Preferably, the lower block comprises a first groove configured to accommodate the suture and a second groove configured to accommodate the double-pointed medical suture needle, wherein the first and second grooves are arranged substantially perpendicularly to each other. Preferably, there is also a lower crimping pin arranged in a lower crimping pin channel at an intercept of the first groove and the second groove. The upper block may comprise an upper crimping pin arranged in an upper crimping pin channel at the intercept of the first groove and the second groove. Preferably, the lower crimping pin and the upper crimping pin are configured to be moved in the lower crimping pin channel and the upper crimping pin channel, respectively, towards the intercept of the first groove and second groove to secure the suture to the double-pointed medical suture needle. As a person skilled in the art would realize, the lower and upper blocks are not necessarily arranged on top of each other. They may have any suitable arrangements in relation to other reference points and could in principle be referred to a first and a second block—the fact that the blocks can be pressed towards each other to lock the double-pointed medical suture needle between them is enough to define the arrangement of the blocks of the crimping device.

The presently disclosed crimping device for securing a suture to a double-pointed medical suture needle provides an efficient, reliable and fast tool for fastening a suture to a needle, which can be used as part of manufacturing process with the aim of supplying pre-packed double-pointed medical suture needles with a suture attached.

The inventors have realized that double-pointed medical suture needles, in particular double-pointed medical suture needles having a through-hole in the needle body for the suture, are associated with challenges related to the attachment of the suture, in particular attachment on an industrial scale. The inventors have therefore developed a crimping device that can secure a suture to a double-pointed medical suture needle efficiently wherein the alignment of the part that deforms the needle and the needle is built into the device.

Double-pointed medical suture needles used in, for example, suturing devices with built-in needle-transfer of the needle between two jaws, may have two indentations, which may be used by the presently disclosed suturing device to hold the needle. The double-pointed medical suture needle does not have to be limited to any specific number of indentations, and may have further indentations, such as 3, 4, 5, 6, 7, 8, 10, 12 or 16 indentations.

The lower crimping pin arranged in a lower crimping pin channel and the upper crimping pin arranged in an upper crimping pin channel have the purpose of deforming the double-pointed medical suture needle at the through-hole when the lower and upper blocks are pressed together. The pins and channels are typically substantially cylindrical, but may have any suitable shape. The lower crimping pin may be configured to slide in the lower crimping pin channel towards and away from the intercept of the first groove and the second groove, i.e. where the double-pointed medical suture needle and suture are placed. An end of the lower crimping pin, such as a pointed end, may deform the double-pointed medical suture needle when it is pushed against it. The contact area between the lower and/or upper crimping pin can be adapted to specific needle and suture sizes dimensions, including the dimensions of the trough-hole of the double-pointed medical suture needles. The upper lower crimping pin may be arranged in the same way: The upper crimping pin may be configured to slide in the upper crimping pin channel towards and away from the intercept of the first groove and the second groove, i.e. where the double-pointed medical suture needle and suture are placed. An end of the upper crimping pin, such as a pointed end, may deform the double-pointed medical suture needle when it is pushed against it. The end may have any shape suitable for performing the deformation, including a substantially tapered, a rounder or a straight end.

Preferably, the lower block and the upper block are adapted to hold the double-pointed medical suture needle in a locked position when the lower block and the upper block are pressed towards each other. This can be done, for example, by having a second groove configured to accommodate the double-pointed medical suture needle and a part of the upper block configured to assert a force on the double-pointed medical suture needle to lock in the second groove.

Figure 7:
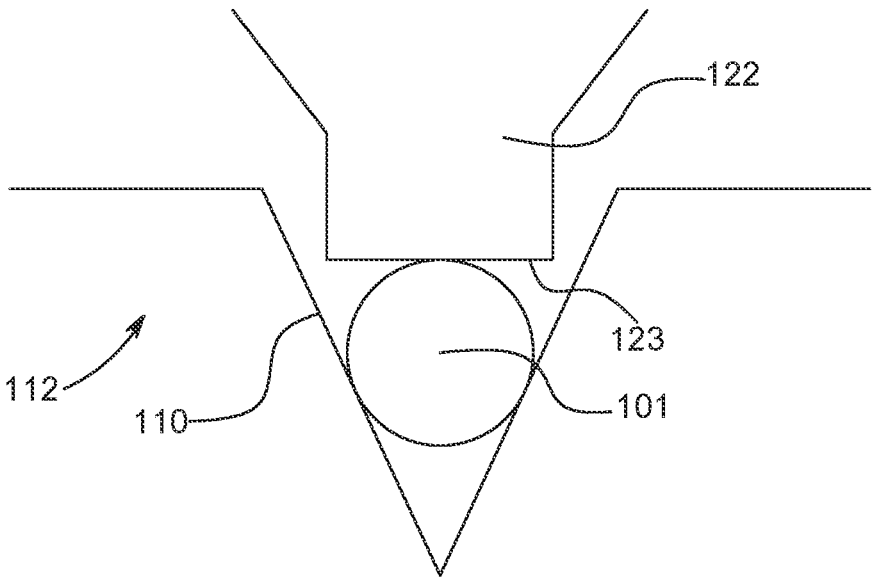
FIG. 7 shows an example of how the double-pointed medical suture needle can be locked between the lower block and the upper block.

FIG. 7 shows an example of how the double-pointed medical suture needle can be locked between the lower block and the upper block. In this example the lower block (112) has a V-shaped second groove (110). FIG. 7 shows a cross-section of the lower block (112), double-pointed medical suture needle (101) and upper block (114). The upper block has a holder element (122) facing the lower block (112). When the upper block, including the holder element (122) is pushed downwardly against the double-pointed medical suture needle (101) in the second groove (110), it locks the double-pointed medical suture needle (101) at the bottom of the V-shaped second groove (110).

Preferably, the at least one needle holder element has a substantially flat side facing the lower block. As a person skilled in the art would realize, the side facing the lower block does, however, not have be completely flat for the principle to work. In the same way the second groove in the lower block may cross-section having a tapered shape being progressively smaller with reference from a side facing the upper block. It may be a V-shape, but other suitable tapered or rounded shapes may also be useful for locking the double-pointed medical suture needle as described.

The at least one needle holder element may be an elongate element adapted to be introduced into the second groove in the lower block when the lower block and the upper block are pressed towards each other.

Preferably, there are at least two needle holder elements, wherein at least one needle holder element is disposed on each side of the upper crimping pin. The elements may be fully integrated in the upper block, which may consequently be made in one piece.

The crimping device may further comprise a secondary lower block arranged on an exterior side of the lower block relative to an interior side comprising the first and second grooves. The lower crimping pin may be fixed to the secondary lower block. When the secondary lower block is pressed towards the lower block, the lower crimping pin may thereby slide in the lower crimping pin channel. The lower crimping pin may be configured such that it causes a deformation of the double-pointed medical suture needle when the lower block and the secondary lower block are pressed together. The crimping device may further comprise a lower spring, such as a disc spring, arranged between the lower block and the secondary lower block. The spring can be configured to provide very precise crimping of the double-pointed medical suture needle. A 'secondary lower block' shall be construed broadly to cover any suitable element for pressing against the lower spring such that the lower crimping pin protrudes from the lower block.

When the secondary lower block is pressed towards the lower block, wherein the lower spring, such as a disc spring, is arranged between the lower block and the secondary lower block, at some point the spring will start becoming compressed. The spring may be adjusted such that when it has reached a compressed state where it cannot be compressed anymore, the end of the lower crimping pin may reach a point where it protrudes from the surface of the lower block towards the double-pointed medical suture needle and deforms the double-pointed medical suture needle as much as needed to crimp the suture to the double-pointed needle. The stiffness of the spring can be adjusted such that the crimping can be done in a controlled manner.

The upper side of the crimping device may be arranged in the same way. Thus, the crimping device may further comprise a secondary upper block arranged on an exterior side of the upper block relative to an interior side facing the lower block. The upper crimping pin may be fixed to the secondary upper block. When the secondary upper block is pressed towards the upper block, the upper crimping pin may thereby slide in the upper crimping pin channel. The upper crimping pin may be configured such that it causes a deformation of the double-pointed medical suture needle when the lower block and the secondary lower block are pressed together. The crimping device may further comprise an upper spring, such as a disc spring, arranged between the upper block and the secondary upper block. The spring can be configured to provide very precise crimping of the double-pointed medical suture needle. When the secondary upper block is moved towards the upper block, wherein the upper spring, such as a disc spring, is arranged between the upper block and the secondary upper block, at some point the spring will start being compressed. The spring may be adjusted such that when it has reached a compressed state where it cannot be compressed anymore, the end of the upper crimping pin may reach a point where it deforms the double-pointed medical suture needle as much as needed to crimp the suture to the double-pointed needle. The stiffness of the spring can be adjusted such that the crimping can be done in a controlled manner. In the same way as the secondary lower block, the 'secondary upper block' shall be construed broadly to cover any suitable element for pressing against the upper spring such that the upper crimping pin protrudes from the upper block FIG. 1 shows an example of a the presently disclosed crimping device (100) for securing a suture (102) to a double-pointed medical suture needle (101). The double-pointed medical suture needle (101) can be placed in the second groove (110) of the lower block (112). The suture (102) can be placed in the first groove (111) of the lower block (112). The lower block (112) has a lower crimping pin channel (119) in which the lower crimping pin (103) can slide. The upper block (114) has an upper crimping pin channel (120) in which the upper crimping pin (104) can slide. Both the lower crimping pin (103) and the upper crimping pin (104) have a pointed end (106) for crimping the double-pointed medical suture needle (101). The crimping device (100) further comprises a secondary lower block (113) and a secondary upper block (115). There is a spring (105) between the lower block (112) and the secondary lower block (113) as well as between the upper block (114) and the secondary upper block (115). The crimping device (100) further comprises four calibration pins (107) for adjustment of crimping positions of the lower crimping pin (103) and/or the upper crimping pin (104). The crimping device (100) further comprises two guide pins (108) and corresponding guide channels (109) for securing that the lower block (113) and the upper block (114) are laterally aligned when they are pressed towards each other.

The double-pointed medical suture needle may be made of any suitable material, typically a metal or metal alloy, such as stainless steel. The double-pointed medical suture needle may be made of a material, for example metal, that can be deformed to reduce the size of the through-hole for the suture to firmly hold the suture. The crimping device may be configured such that the crimping pins cause a deformation of the double-pointed medical suture needle to bond the suture to the double-pointed medical suture needle when the lower block and the upper block are pressed towards each other.

Figure 2:
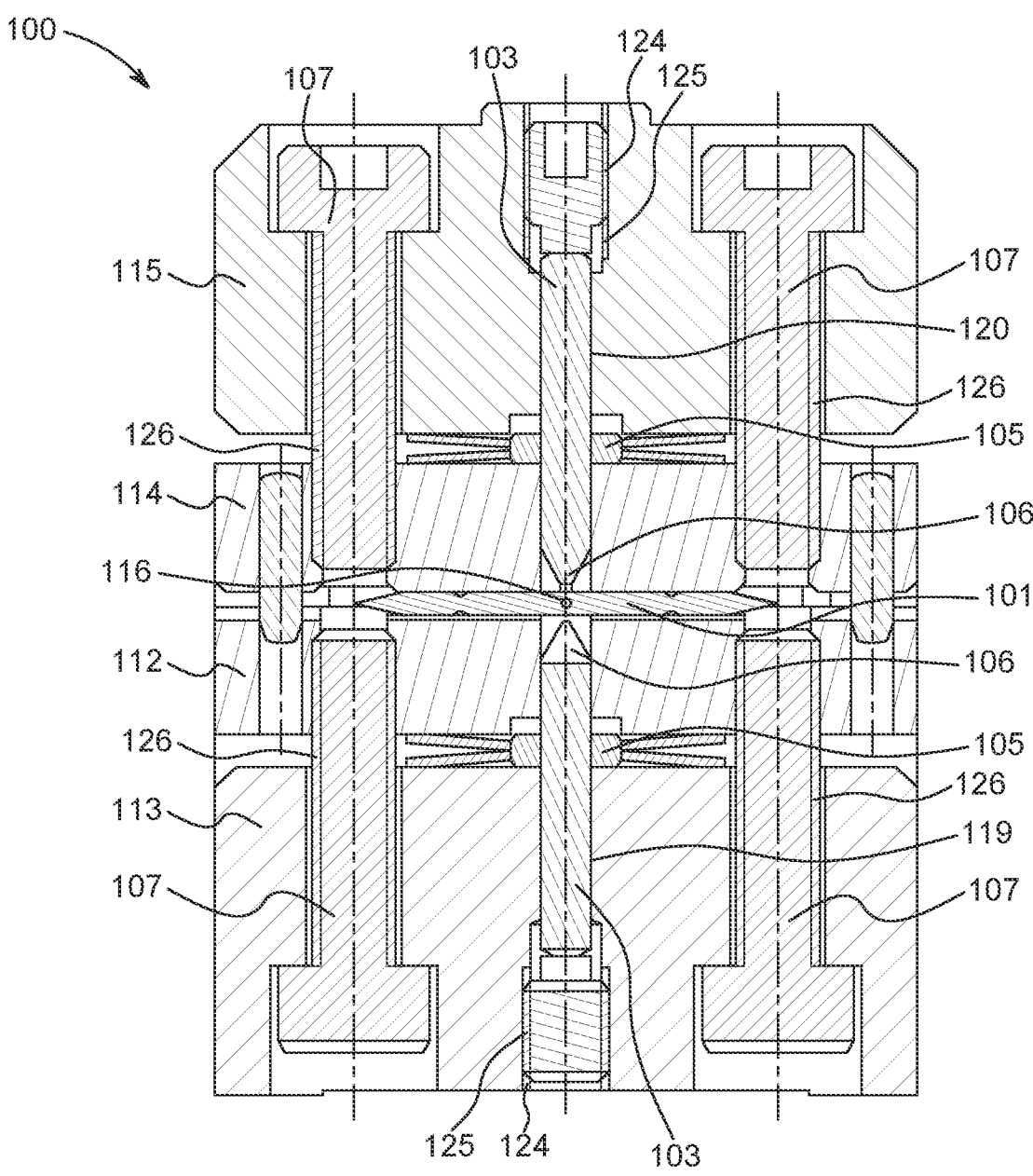
FIG. 2 shows a further example of a the presently disclosed crimping device.

FIG. 2 shows a further example of a the presently disclosed crimping device (100) for securing a suture to a double-pointed medical suture needle (101). The double-pointed medical suture needle (101) can be placed in the second groove of the lower block (112). The suture (102) can be placed in the first groove (111) of the lower block (112). The lower block (112) has a lower crimping pin channel (119) in which the lower crimping pin (103) can slide. The upper block (114) has an upper crimping pin channel (120) in which the upper crimping pin (104) can slide. Both the lower crimping pin (103) and the upper crimping pin (104) have a pointed end (106) for crimping the double-pointed medical suture needle (101). The crimping device (100) further comprises a secondary lower block (113) and a secondary upper block (115). There is a spring (105) between the lower block (112) and the secondary lower block (113) as well as between the upper block (114) and the secondary upper block (114). The crimping device (100) further comprises four calibration pins (107) for adjustment of crimping positions of the lower crimping pin (103) and/or the upper crimping pin (104).

In the example of FIG. 2 the lower crimping pin (103) have first threads (124) engaging with second threads (125) of the secondary lower block (113) respectively. The first threads may be threads of the lower crimping pin (103) itself or, alternatively, the lower crimping pin (103) may include a separate part, such as a set screw, which can have the first threads (124). The set screw may in this regard be seen as a part that belongs to the crimping pin. A person skilled in the art realizes that both implementations are possible and covered by the language stating that the crimping pin comprises first threads. In case the lower crimping pin (103) includes a separate lower set screw, the set screw can act as an element that blocks the lower crimping pin (103) from moving away from the double-pointed medical suture needle, downwards in the example of FIG. 2. The arrangement can be used to calibrate a vertical fixation or blocking point of the lower crimping pin (103) with respect to the secondary lower block (113). By screwing the lower crimping pin (103), or a set screw, a vertical fixation point to the secondary lower block (113), or a lower blocking point in the secondary lower block (113) can be adjusted. The upper crimping pin (103) and the secondary upper block (115) may have the same mechanism. This means that the upper crimping pin (103) itself or a separate upper set screw may comprise the first threads (124).

According to one embodiment of the presently disclosed crimping device for securing a suture to a double-pointed medical suture needle, the second groove is substantially straight. The first groove may also be substantially straight.

Each of the lower and upper crimping pins may have a pointed end towards the intercept of the first groove and second groove. The pointed end may be configured to cause a deformation of the double-pointed medical suture needle to bond the suture to the double-pointed medical suture needle when the lower and upper crimping pins are moved to the intercept of the first groove and second groove.

Figure 3:
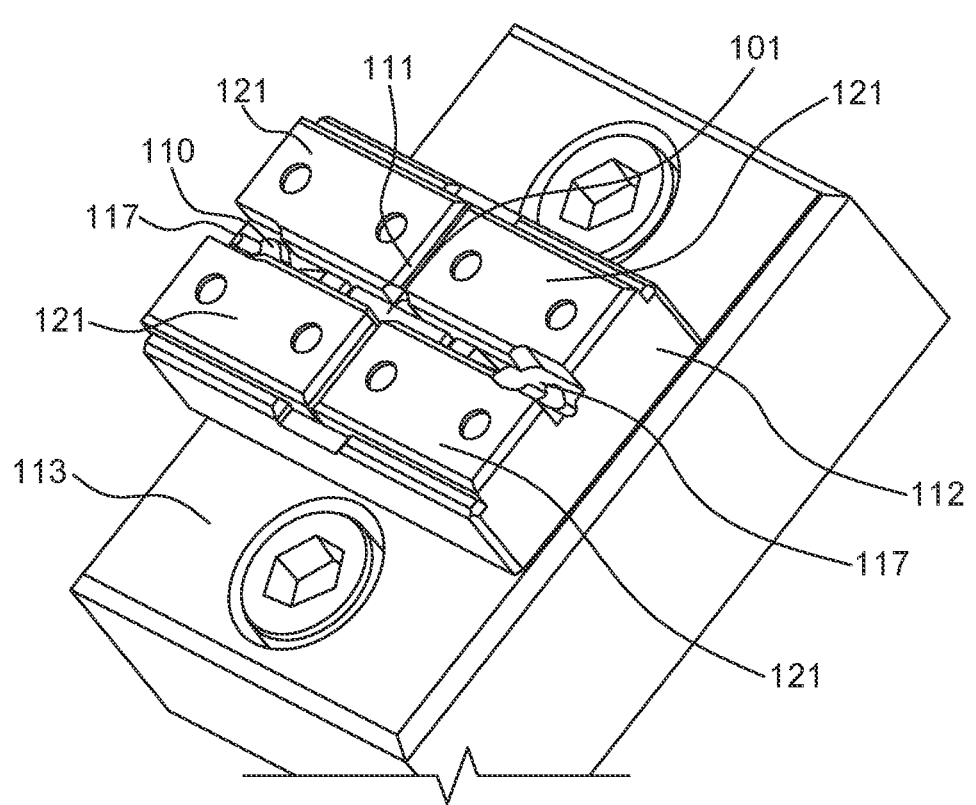
FIG. 3 shows an example of a lower block.

The lower block may comprise four sub-block arranged to form two substantially perpendicular gaps forming the first groove and the second groove. As would be recognized by a person skilled in the art, a 'block' is not necessarily a single solid block but may, as shown, comprise a number of sub-blocks forming the gaps. The sub-blocks can either be part of a solid block or separate smaller blocks. It is understood that they form a 'block' in the context of the presently disclosed crimping device in either of these embodiments. The four sub-block may be spaced to form the first groove and the second groove. FIG. 3 shows an example of such a lower block (112), wherein four sub-blocks (121) form a first groove (111) and a second groove (110). The lower block (112) has two free spaces (117) around each end of the positioned double-pointed medical suture needle (101). A secondary lower block (113) is disposed on an exterior side of the lower block (112) relative to the side where the double-pointed medical suture needle (101) is placed.

Figure 4A:
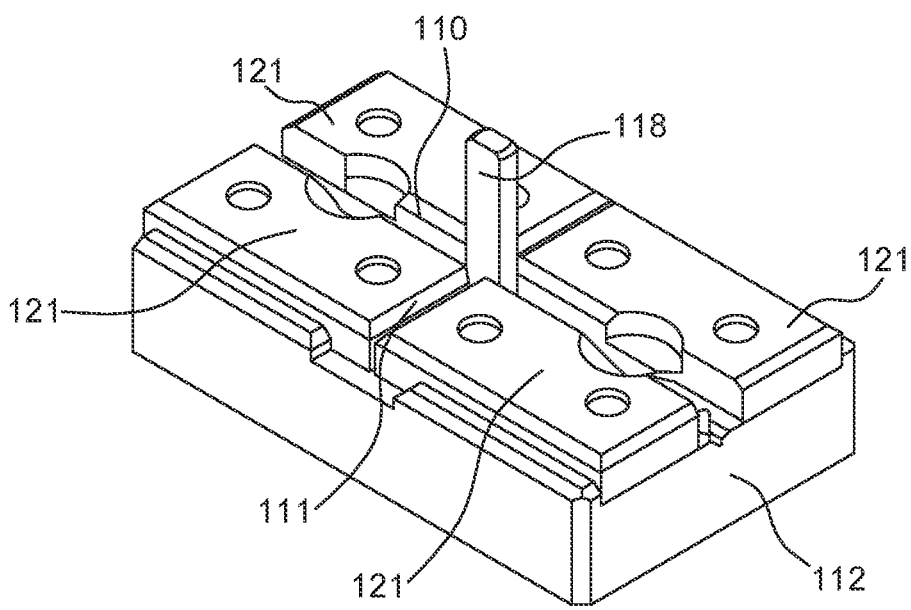
FIG. 4A shows a further example of a lower block with a gap adjustment element.
Figure 4B:
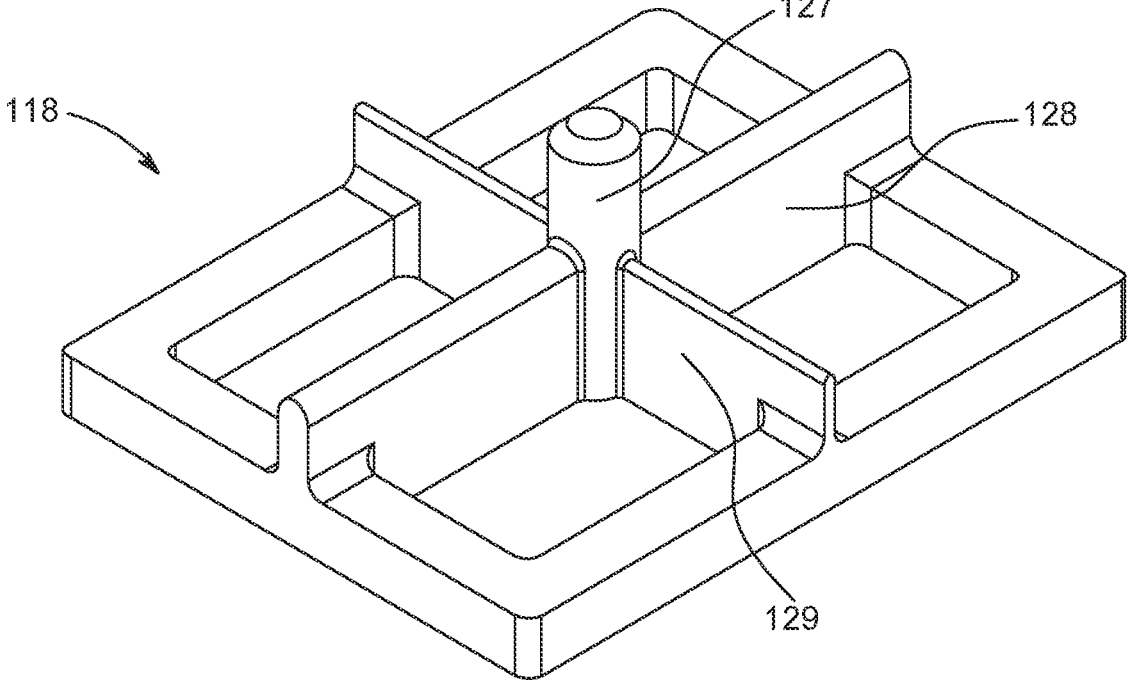
FIG. 4B shows an alternative gap adjustment element.
Figure 5:
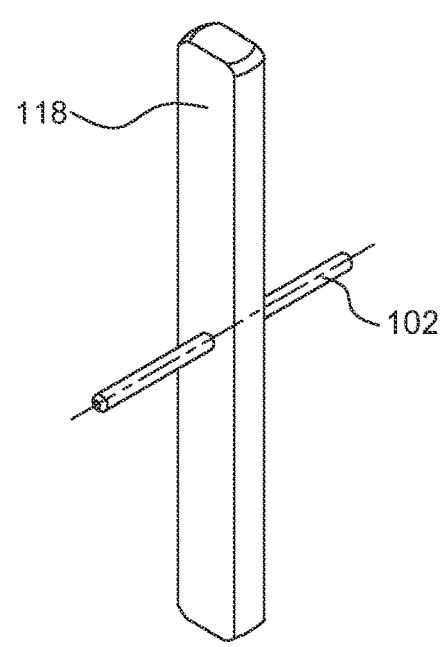
FIG. 5 shows an example of an adjustment element for adjusting the gap between the sub-blocks of the lower block.

The crimping device may further comprise an adjustment element for adjusting the gap between the sub-blocks corresponding to the first groove and or adjusting the gap between the sub-blocks corresponding to the second groove. The adjustment element may comprise an elongate pin adapted to be inserted into the first groove at the intercept of the first groove and second groove, the adjustment element comprising a through-hole for the suture. FIG. 4A shows an example of a lower block (112), wherein an adjustment element (118) is placed in the second first groove (111). FIG. 4B shows an example of a gap adjustment element (118), which includes a gap adjustment guide (127) that can be inserted into the lower crimping pin channel, a needle gap adjustment element (128) that can adjust the gap for the needle in the lower block (112) and a suture gap adjustment element (129) that can adjust the gap for the suture in the lower block (112). FIG. 5 shows a further example of an adjustment element (118) for adjusting the gap between the sub-blocks of the lower block.

The crimping device may further comprise one or more guide pins in one of the lower block and the upper block. Preferably, the other one of the lower block and the upper block comprises one or more corresponding guide channels. The guide pins and guide channels may be configured to ensure that the lower block and the upper block are laterally aligned when they are pressed towards each other.

In one embodiment of the presently disclosed crimping device for securing a suture to a double-pointed medical suture needle, at least one, preferably both, of the lower block and the upper block comprises at least one, preferably at least two, calibration pins adapted to adjust compressed and/or decompressed positions of the lower and upper springs. The lower crimping pin and/or the upper crimping pin may have calibration pin threads engaging with corresponding calibration pin channel threads in the lower block and upper block respectively. This mechanism can be used to calibrate the individual positions of the lower and upper springs.

Figure 6:
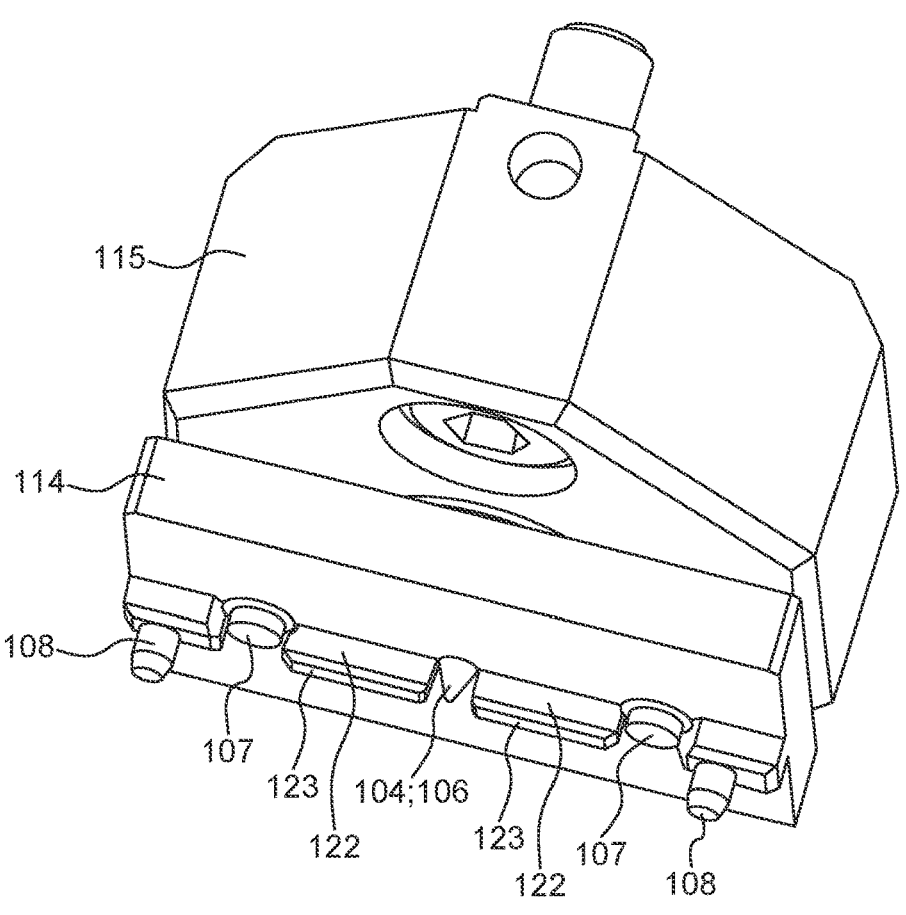
FIG. 6 shows an example of an upper block.

An example of calibration pins (107) is shown in FIG. 1. The calibration pins may be fixed to the secondary lower block and secondary upper block, respectively. In the example of FIG. 1 the calibration pins (107) have calibration pin threads (126) engaging with corresponding calibration pin channel threads in the lower block (112) and upper block (114) respectively. They may be used to adjust compressed and/or decompressed positions of the lower and upper springs. The compressed state of the lower and upper springs correspond to the state wherein the lower crimping pin and upper crimping pin deform the double-pointed medical suture needle. The calibration pins may be screws that adjust the distance between the lower block and secondary lower block and the upper block and the secondary upper block, respectively, when the lower spring and the upper springs are in a decompressed state. The calibration pins may be screws that adjust the distance between the lower block and secondary lower block and the upper block and the secondary upper block, respectively, in a crimping configuration, i.e. how close the blocks can get to each other. In FIG. 6, which shows an example of an upper block, there are two visible calibrations pins (107). In the same figure there are two guide pins (108) in the upper block (114).

The lower block and/or the upper block may have suture side openings for the suture, as shown in, for example, FIG. 3. One advantage of having these openings is that one long suture can be threaded through many double-pointed medical suture needles in a crimping process for a plurality of double-pointed medical suture needles. The needles can then be crimped one by one in the crimping device. When a needle has been crimped it can move on to a suture length adjustment and cutting procedure. The crimping device may, accordingly, further comprise a cutting mechanism for cutting the suture and/or a suture length adjustment elements and/or a winding mechanism for winding the suture. The crimping device may further comprise one or more suture length adjustment elements. The crimping device may further comprise a holding and pressing mechanism for pressing the lower block and the upper block, and/or for pressing the secondary lower block and the secondary upper block towards each other. The crimping device may further comprise a lever for holding and exerting a force to the holding and pressing mechanism for pressing the lower block and the upper block, and/or for pressing the secondary lower block and the secondary upper block towards each other.

Figure 8:
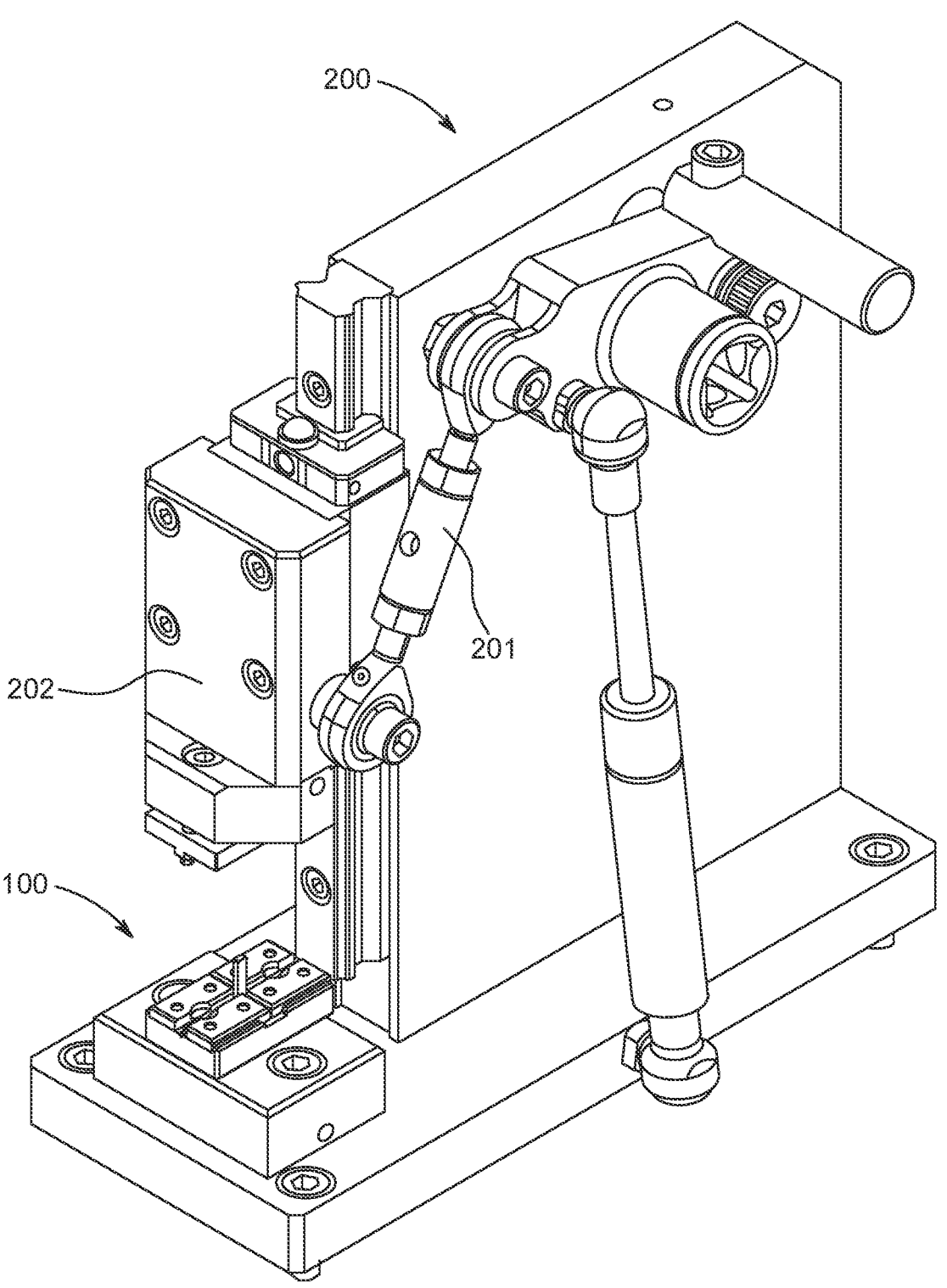
FIG. 8 shows an example of a crimping system comprising a crimping device, a holding and pressing mechanism and a lever.

FIG. 8 shows an embodiment of the presently disclosed crimping system (200) comprising a crimping device (100). The crimping device (100) comprises a lower block and an upper block that can be pressed towards each other using a holding and pressing mechanism (202) and a lever (201).

The present disclosure further relates to a method of securing at least one suture to at least one double-pointed medical suture needle, comprising the steps of:

threading the double-pointed medical suture needle by inserting the suture through a through-hole of the double-pointed medical suture needle;

providing a crimping device having a lower block and an upper block, wherein the lower block comprises a lower crimping pin arranged in a lower crimping pin channel at an intercept of the first groove and the second groove and the upper block comprises an upper crimping pin arranged in an upper crimping pin channel at an intercept of the first groove and the second groove;

placing the double-pointed medical suture needle in the second groove and the suture in the first groove; and crimping the double-pointed medical suture needle by moving the lower block and the upper block together and pushing the lower crimping pin and the upper crimping pin against and deforming the double-pointed medical suture needle to secure the suture to the double-pointed medical suture needle.

The method may be performed using any embodiment of the presently disclosed crimping device for securing a suture to a double-pointed medical suture needle.

The process of securing the at least one suture to at least one double-pointed medical suture needle can be performed according to the following, non-limiting, example. Before the crimping begins the suture is inserted through a through-hole of the double-pointed medical suture needle. Initially the crimping device is in an open configuration wherein the lower block and the upper block are separated. In the open configuration the double-pointed medical suture needle can be placed in the second groove and the suture in the first groove. The lower and upper springs are in a decompressed state. The lower block and the upper block are then moved together, which, in a first step, when the lower block and the upper contact get in contact, locks the double-pointed medical suture needle in a stable position between the lower block and upper block. If the lower block and the upper block are then further pressed against each other, the lower and upper springs will begin to compress, which will make the lower crimping pin and the upper crimping pin protrude from the lower block and upper block, respectively. This will cause the double-pointed medical suture needle to deform at the suture. The deformation secures the suture to the double-pointed medical suture needle in a controlled and precise manner.

The method may further comprise the step of pressing a secondary lower block arranged on an exterior side of the lower block relative to an interior side comprising the first and second grooves, to which the lower crimping pin is fixed, and a secondary upper block arranged on an exterior side of the upper block relative to an interior side arranged towards the lower block, to which the upper crimping pin is fixed, towards each other. This can be illustrated, for example, by FIG. 1. If the secondary lower block (113) and the secondary upper block (115) are pressed towards each other, i.e. towards the needle, it will also mean that they will press the lower block (112) and the upper block (114) towards each other. If the lower crimping pin (103) is fixed to the secondary lower block (113) and the upper crimping pin (104) is fixed to the secondary upper block (115), it will cause the lower crimping pin (103) and the upper crimping pin (104) to deform the double-pointed medical suture needle (101) at the through-hole (116) for the suture (102).

The method may further comprise the step of cutting the suture, adjusting the suture length and/or winding the suture. The method may also operate in a serial crimping procedure of a plurality of double-pointed medical suture needles. In this procedure the plurality of double-pointed medical suture needles may be threaded using the same suture, wherein the double-pointed medical suture needles are crimped one by one, and wherein the suture is winded and cut for each crimping.

List of Elements in Figures

100—crimping device
101—double-pointed medical suture needle
102—suture
103—lower crimping pin
104—upper crimping pin
105—lower and upper springs
106—pointed end
107—calibration pins
108—guide pins
109—guide channels
110—second groove 111—first groove
112—lower block
113—secondary lower block
114—upper block
115—secondary upper block
116—through-hole
117—free space
118—adjustment element
119—lower crimping pin channel
120—upper crimping pin channel
121—sub-blocks
122—holder element
123—substantially flat side
124—first threads
125—second threads
126—calibration pin threads
127—gap adjustment guide
128—needle gap adjustment element
129—suture gap adjustment element
200—crimping system
201—lever
202—holding and pressing mechanism

Further Details of the Invention

A crimping device for securing a suture to a double-pointed medical suture needle, the crimping device comprising:

a lower block and an upper block that can be pressed towards each other to secure the suture to the double-pointed medical suture needle, the lower block comprising:

a first groove configured to accommodate the suture;

a second groove configured to accommodate the double-pointed medical suture needle, the first and second grooves arranged substantially perpendicularly to each other, wherein the lower block comprises a lower crimping pin arranged in a lower crimping pin channel at an intercept of the first groove and the second groove;

wherein the upper block comprises an upper crimping pin arranged in an upper crimping pin channel at the intercept of the first groove and the second groove;

wherein the lower crimping pin and the upper crimping pin are configured to be moved in the lower crimping pin channel and the upper crimping pin channel, respectively, towards the intercept of the first groove and second groove to secure the suture to the double-pointed medical suture needle.

The crimping device according to item 1, wherein the lower and upper crimping pin each have a pointed end towards the intercept of the first groove and second groove.

The crimping device according to item 2, wherein the pointed end causes a deformation of the double-pointed medical suture needle to bond the suture to the double-pointed medical suture needle when the lower and upper crimping pins are moved to the intercept of the first groove and second groove.

The crimping device according to any one of the preceding items, wherein the lower block and the upper block are adapted to hold the double-pointed medical suture needle in a locked position when the lower block and the upper block are pressed towards each other.

The crimping device according to any one of the preceding items, wherein the second groove in the lower block has cross-section having a tapered shape being progressively smaller with reference from a side facing the upper block, preferably wherein the cross-section is substantially V-shaped.

The crimping device according to any one of the preceding items, wherein the upper block comprises at least one needle holder element facing the lower block, adapted to lock the double-pointed medical suture needle in a locked position when the lower block and the upper block are pressed towards each other.

The crimping device according to item 6, wherein the at least one needle holder element has a substantially flat side facing the lower block . . .

The crimping device according to any one of items 6-7, wherein the at least one needle holder element is an elongate element adapted to be introduced into the second groove in the lower block when the lower block and the upper block are pressed towards each other.

The crimping device according to any one of items 6-8, comprising at least two needle holder elements, wherein at least one needle holder element is disposed on each side of the upper crimping pin.

The crimping device according to any one of the preceding items, further comprising a secondary lower block arranged on an exterior side of the lower block relative to an interior side comprising the first and second grooves.

The crimping device according to item 10, wherein the lower crimping pin is fixed to the secondary lower block.

The crimping device according to any one of items 10-11, further comprising a lower spring, such as a disc spring, arranged between the lower block and the secondary lower block.

The crimping device according to any one of items 10-12, wherein the lower crimping pin causes a deformation of the double-pointed medical suture needle when the lower block and the secondary lower block are pressed together.

The crimping device according to any one of the preceding items, further comprising a secondary upper block arranged on an exterior side of the upper block relative to an interior side arranged towards the lower block.

The crimping device according to item 14, wherein the upper crimping pin is fixed to the secondary upper block.

The crimping device according to any one of items 14-15, further comprising an upper spring, such as a disc spring, arranged between the upper block and the secondary upper block.

The crimping device according to any one of items 14-16, wherein the upper crimping pin causes a deformation of the double-pointed medical suture needle when the upper block and the secondary upper block are pressed together.

The crimping device according to any one of the preceding items, wherein one of the lower block and the upper block comprises one or more guide pins and the other of the lower block and the upper block comprises one or more corresponding guide channels.

The crimping device according to any one of the preceding items, wherein at least one, preferably both, of the lower block and the upper block comprises at least one, preferably at least two, calibration pins for adjustment of crimping positions of the lower crimping pin and/or the upper crimping pin.

The crimping device according to any one of the preceding items, wherein the lower block comprises four sub-block arranged to form two substantially perpendicular gaps forming the first groove and the second groove.

The crimping device according to item 20, further comprising an adjustment element for adjusting the gap between the sub-blocks corresponding to the first groove and/or the gap between the sub-blocks corresponding to the second groove.

The crimping device according to item 21, wherein the adjustment element comprises an elongate pin adapted to be inserted into the first groove at the intercept of the first groove and second groove, the adjustment element comprising a through-hole for the suture.

The crimping device according to any one of the preceding items, further comprising a cutting mechanism for cutting the suture.

The crimping device according to any one of the preceding items, further comprising a winding mechanism for winding the suture and/or one or more suture length adjustment elements.

The crimping device according to any one of the preceding items, further comprising holding and pressing mechanism for pressing the lower block and the upper block, and/or for pressing the secondary lower block and the secondary upper block towards each other.

The crimping device according to item 25, further comprising a lever for holding and exerting a force to the holding and pressing mechanism for pressing the lower block and the upper block, and/or for pressing the secondary lower block and the secondary upper block towards each other.

A method of securing at least one suture to at least one double-pointed medical suture needle, comprising the steps of:

threading the double-pointed medical suture needle by inserting the suture through a through-hole of the double-pointed medical suture needle;

providing a crimping device having a lower block and an upper block, wherein the lower block comprises a lower crimping pin arranged in a lower crimping pin channel at an intercept of the first groove and the second groove and the upper block comprises an upper crimping pin arranged in an upper crimping pin channel at an intercept of the first groove and the second groove;

placing the double-pointed medical suture needle in the second groove and the suture in the first groove; and crimping the double-pointed medical suture needle by moving the lower block and the upper block together and pushing the lower crimping pin and the upper crimping pin against and deforming the double-pointed medical suture needle to secure the suture to the double-pointed medical suture needle.

The method of securing at least one suture to at least one double-pointed medical suture needle according to item 27, comprising the step of pressing a secondary lower block arranged on an exterior side of the lower block relative to an interior side comprising the first and second grooves, to which the lower crimping pin is fixed, and a secondary upper block arranged on an exterior side of the upper block relative to an interior side arranged towards the lower block, to which the upper crimping pin is fixed, towards each other.

The method of securing at least one suture to at least one double-pointed medical suture needle according to any one of items 27-28 using the crimping device according to any one of items 1-26.

The invention claimed is:

1. A crimping device for securing a suture to a double-pointed medical suture needle, the crimping device comprising:

a lower block and an upper block that can be pressed towards each other to secure the suture to the double-pointed medical suture needle, the lower block comprising:

a first groove configured to accommodate the suture;

a second groove configured to accommodate the double-pointed medical suture needle, the first and second grooves arranged substantially perpendicularly to each other, wherein the lower block comprises a lower crimping pin arranged in a lower crimping pin channel at an intercept of the first groove and the second groove;

wherein the upper block comprises an upper crimping pin arranged in an upper crimping pin channel at the intercept of the first groove and the second groove;

wherein the lower crimping pin and the upper crimping pin are configured to be moved in the lower crimping pin channel and the upper crimping pin channel, respectively, towards the intercept of the first groove and second groove to secure the suture to the double-pointed medical suture needle;

wherein the upper block comprises at least one needle holder element facing the lower block, adapted to lock the double-pointed medical suture needle in a locked position when the lower block and the upper block are pressed towards each other.

2. The crimping device according to claim 1, wherein the lower and upper crimping pin each have a pointed end towards the intercept of the first groove and second groove, wherein the pointed end causes a deformation of the double-pointed medical suture needle to bond the suture to the double-pointed medical suture needle when the lower and upper crimping pins are moved to the intercept of the first groove and second groove.

3. The crimping device according to claim 1, wherein the lower block and the upper block are adapted to hold the double-pointed medical suture needle in a locked position when the lower block and the upper block are pressed towards each other.

4. The crimping device according to claim 1, wherein the second groove in the lower block has cross-section having a tapered shape being progressively smaller with reference from a side facing the upper block.

5. The crimping device according to claim 1, wherein the at least one needle holder element has a substantially flat side facing the lower block.

6. The crimping device according to claim 1, wherein the at least one needle holder element is an elongate element adapted to be introduced into the second groove in the lower block when the lower block and the upper block are pressed towards each other.

7. The crimping device according to claim 1, wherein the at least one needle holder element comprises at least two needle holder elements, wherein one needle holder element is disposed on each side of the upper crimping pin.

8. The crimping device according to claim 1, further comprising a secondary lower block arranged on an exterior side of the lower block relative to an interior side comprising the first and second grooves, wherein the lower crimping pin is fixed to the secondary lower block.

9. The crimping device according to claim 8, further comprising a lower spring arranged between the lower block and the secondary lower block.

10. The crimping device according to claim 8, wherein the lower crimping pin causes a deformation of the double-pointed medical suture needle when the lower block and the secondary lower block are pressed together.

11. The crimping device according to claim 8, wherein the lower crimping pin is configurable to a fixed position relative to the secondary lower block.

12. The crimping device according to claim 8, wherein the lower crimping pin comprises first threads engaging with corresponding second threads of the secondary lower block, or wherein the lower crimping pin comprises a lower set screw having first threads engaging with corresponding second threads of the secondary lower block.

13. A method of securing at least one suture to at least one double-pointed medical suture needle, comprising the steps of:

threading the double-pointed medical suture needle by inserting the suture through a through-hole of the double-pointed medical suture needle;

providing a crimping device having a lower block and an upper block, wherein the lower block comprises a lower crimping pin arranged in a lower crimping pin channel at an intercept of a first groove and a second groove and the upper block comprises an upper crimping pin arranged in an upper crimping pin channel at an intercept of the first groove and the second groove;

placing the double-pointed medical suture needle in the second groove and the suture in the first groove;

crimping the double-pointed medical suture needle by moving the lower block and the upper block together and pushing the lower crimping pin and the upper crimping pin against and deforming the double-pointed medical suture needle to secure the suture to the double-pointed medical suture needle; and pressing the lower block and the upper block against each other such that a lower spring between the lower block and a secondary lower block, to which the lower crimping pin or a lower set screw of the lower crimping pin is fixed, is compressed and the lower crimping pin protrudes from the lower block, and such that an upper spring between the upper block and a secondary upper block, to which the upper crimping pin or an upper set screw of the upper crimping pin is fixed, is compressed and the upper crimping pin protrudes from the upper block.

14. A crimping device for securing a suture to a double-pointed medical suture needle, the crimping device comprising:

a lower block and an upper block that can be pressed towards each other to secure the suture to the double-pointed medical suture needle, the lower block comprising:

a first groove configured to accommodate the suture;

a second groove configured to accommodate the double-pointed medical suture needle, the first and second grooves arranged substantially perpendicularly to each other, wherein the lower block comprises a lower crimping pin arranged in a lower crimping pin channel at an intercept of the first groove and the second groove;

wherein the upper block comprises an upper crimping pin arranged in an upper crimping pin channel at the intercept of the first groove and the second groove;

wherein the lower crimping pin and the upper crimping pin are configured to be moved in the lower crimping pin channel and the upper crimping pin channel, respectively, towards the intercept of the first groove and second groove to secure the suture to the double-pointed medical suture needle, further comprising a secondary upper block arranged on an exterior side of the upper block relative to an interior side arranged towards the lower block, wherein the upper crimping pin is fixed to the secondary upper block.

15. The crimping device according to claim 14, further comprising an upper spring arranged between the upper block and the secondary upper block.

16. The crimping device according to claim 14, wherein the upper crimping pin causes a deformation of the double-pointed medical suture needle when the upper block and the secondary upper block are pressed together.

17. The crimping device according to claim 14, wherein the upper crimping pin is configurable to a fixed position relative to the secondary upper block.

18. The crimping device according to claim 14, wherein the upper crimping pin comprises first threads engaging with corresponding second threads of the secondary upper block, or wherein the upper crimping pin comprises an upper set screw having first threads engaging with corresponding second threads of the secondary upper block.

* * * * *